(12) United States Patent
Elist

(10) Patent No.: US 6,475,137 B1
(45) Date of Patent: Nov. 5, 2002

(54) SUBCUTANEOUS PENILE IMPLANT

(76) Inventor: James Elist, 9033 Wilshire Blvd., Suite 300, Beverly Hills, CA (US) 90211

( * ) Notice: Subject to any disclaimer, the term of this patent is extended or adjusted under 35 U.S.C. 154(b) by 0 days.

(21) Appl. No.: 09/687,741

(22) Filed: Oct. 13, 2000

(51) Int. Cl.[7] ................................................ A61F 2/26
(52) U.S. Cl. ..................................... 600/40; 623/23.67
(58) Field of Search ........................... 623/11.11, 23.67; 600/38, 40

(56) References Cited

U.S. PATENT DOCUMENTS

| 3,893,456 | A | | 7/1975 | Small et al. | |
|---|---|---|---|---|---|
| 4,204,530 | A | | 5/1980 | Finney | |
| 4,267,829 | A | * | 5/1981 | Burton et al. | 128/79 |
| 4,566,446 | A | | 1/1986 | Fogarty | |
| 4,773,403 | A | * | 9/1988 | Daly | 128/79 |
| 4,881,530 | A | * | 11/1989 | Trick | 128/79 |
| 5,063,914 | A | | 11/1991 | Cowen | |
| 5,101,813 | A | * | 4/1992 | Trick | 600/40 |
| 5,250,020 | A | * | 10/1993 | Bley | 600/40 |
| 5,263,981 | A | * | 11/1993 | Polyak et al. | 623/12 |
| 5,344,388 | A | * | 9/1994 | Maxwell et al. | 600/40 |
| 5,611,515 | A | | 3/1997 | Benderev et al. | |
| 5,895,424 | A | * | 4/1999 | Steele, Sr. et al. | 623/11 |
| 5,899,849 | A | | 5/1999 | Elist | |

* cited by examiner

Primary Examiner—Bruce Snow
(74) Attorney, Agent, or Firm—Gene Scott-Patent Law & Venture Group

(57) ABSTRACT

A prosthesis device is designed to be subcutaneously implanted into a penis above the corpus cavernosum and extending from the base of the penis to the glans penis. The prosthesis device contains one or more inflatable tubes for enabling an erectile function of the penis, and these are covered by a shaped body for enabling an improved appearance, texture and size to the penis. Integral with the tubes is a base which is mounted to the pubic bone. The invention includes a manual pump preferably implanted into the scrotum and interconnected with the base by a flexible conduit to inflate the tubes. A fluid is pumped into the inflatable tubs for pressurization thereof so as to cause the the penis to become erect. The tubes are directed upwardly in positional orientation so as to enable the penis to move in a more natural manner.

5 Claims, 3 Drawing Sheets

SUBCUTANEOUS PENILE IMPLANT

BACKGROUND OF THE INVENTION

1. Field of the Invention

This invention relates generally to a penile prosthesis for improved function and appearance, and more particularly to a subcutaneous penile implantation system that may be reversed without permanent tissue damage to the patient.

2. Description of Related Art

The following art defines the present state of this field:

Small et al, U.S. Pat. No. 3,893,456 describes a prosthesis for implantation in the penis to provide a flaccid penis with rigidified dimensions of length and of width, and with the property of flexural stiffness. The prosthesis is used in pairs, each of which is a one-piece member that includes a composite rod having a dimension of axial length and, for the major proportion of its length, is composed of two physically distinct bodies which are integrally joined to each other, one of which is more resistant to bending and to compressive deformation than the other, and a prong extending from said rod, said prong decreasing in lateral cross-section as it extends away from the rod. One of the bodies is stiffly flexible. In the preferred embodiment of the invention, the first of the bodies is a tube of solid material having an inner wall and an outer wall, the inner wall defining an axially extending cavity, the second body filling the cavity, the said first body being the one which is stiffly flexible. The second body is preferably made of a gel or of a foam.

Finney, U.S. Pat. No. 4,204,530 discloses an implantable sleeve for increasing the penile diameter. The sleeve includes a flexible sheet of soft, physiologically acceptable implantable material, the sheet being of sufficient length when formed in the general shape of a cylindrical sleeve to extend from the glans penis to the base of the penis, and of a width which is insufficient to completely encircle the penis, but sufficient to cover the corpora cavernosa. The sheet preferably has edges which are rounded and tapered side edges. The sleeve also includes suturing strips on the inside wall of the sleeve, adjacent the side edges of the sheet, which facilitate the suturing of the sheet to the tunica albuginea. The sleeve further includes porous patches located on the interior of the inside wall of the sleeve into which fibroblasts from the underlying tissues can grow to further anchor the sleeve to the tunica albuginea. In the preferred embodiment, the sheet is of very soft, medical grade silicone elastomer, and suturing strips are of Dacron (tm) fabric and the porous patches are of Dacron(tm) fabric or fluff.

Fogarty, U.S. Pat. No. 4,566,446 describes a penile prosthesis which is adapted for surgical implantation including a pair of fluid fillable prosthetic members and a fluid reservoir containing a supply of the fluid. A pump pumps fluid from the reservoir to the prosthetic members. The pump includes a valving section which is fluidly connected with the reservoir and the prosthetic members, and a pumping section for pumping the fluid from the reservoir to the prosthetic members. The valving section includes a deformable housing with a supply inlet passage fluidly connected to the reservoir and two outlet passages, each outlet passage fluidly connected to a corresponding prosthetic member. Each passage has a check valve for directing the flow of fluid from the reservoir, through the pumping section and into the prosthetic members. When the valving section is manually deformed, the check valves are placed in an inoperable state permitting flow of the fluid from the prosthetic member, through the pumping section, and back into the reservoir.

Cowen, U.S. Pat. No. 5,063,914 describes an apparatus for the treatment of male impotence. The apparatus has a cylinder of a biocompatible polymer which is implanted in the corpus cavernosum of the penis. The cylinder is attached at its proximal end to a base mount which is implanted in the pelvic area. In the flaccid state, the cylinder is empty and limp, and a spring within the cylinder folds the cylinder wall in upon itself to decrease its effective length. Fluid is pumped into the cylinder causing it to stiffen in the erect state. The effective length of the cylinder is increased by the addition of the fluid which compresses the internal spring and unfolds the cylinder. In this manner, the length of the penis is increased from the flaccid to the erect state.

Benderev et al., 5,611,515 describes the surgical treatment of stress urinary incontinence. The disclosed methods include: 1) a technique of probe passage to avoid injuring the bladder and to provide a more accurate and reproducible capture of the pubocervical fascia lateral to the bladder neck and urethra, 2) anchor fixation of the suspending sutures to the pubic bone to decrease the risk of suture pull through from above and to decrease post-operative pain and 3) a simple and reproducible technique to set a limited tension of the suspending sutures. A description of these methods and results of procedures with some of these methods are disclosed. Novel drill guides, suture passers, suture tensioners, and various related tools and devices for use in the surgical method are also disclosed.

Elist, U.S. Pat. No. 5,899,849 describes a penile prosthesis device and a method for surgical installation. The prosthesis device is designed to be subcutaneously implanted into a penis above the corpus cavernosum and extending from the base of the penis to the glans penis. The prosthesis device contains one or more inflatable tubular sacks for enabling an erectile function of the penis, and these are covered by a shaped body for enabling an improved appearance, texture and size to the penis. Integral with the tubular sack is a base which is sutured to the pubic bone. The invention includes a manual pump preferably implanted into the scrotum and interconnected with the base means by a tube, used to inflate the tubular sacks. A fluid is pumped by the pump through the tube, through the base, and into the inflatable tubular sacks for pressurization thereof so as to cause the tubular sacks to achieve rigidity, thereby causing the penis to become erect. If the pump is not large enough to contain enough fluid to inflate the inflatable tubular sack, the invention includes a reservoir that feeds into the pump.

The prior art teaches a device similar to the present invention in the Elist reference, 5,899,849. However, the present invention is an improvement thereof. The improvement includes an improved mounting apparatus for attachment of the invention to the bone structure of the patient, an improvement in the structure of the prosthesis making it easier to attach, and also includes an improved operational orientation of the penile implant portion of the apparatus for superior function with respect to the '849 apparatus. The prior art does not teach these improvements.

SUMMARY OF THE INVENTION

The present invention teaches certain benefits in construction and use which give rise to the objectives described below.

The present invention provides a penile prosthesis device designed to be subcutaneously implanted into the penis and attached to the pubic bone. The device provides a pair of inflatable tubular members enabling an erectile function of the penis. A shaped body portion enables improvements in appearance, texture and size of the penis. Integral with the tubular members is a base for mounting the device to a mounting plate which is, in turn, attached to the pubic bone. The invention also includes a manual pump implanted into the scrotum and interconnected with the base via a flexible tube. This is used to inflate the tubular members. A fluid is pumped through the tube, into the base, and thus into the inflatable tubular members for pressurization thereof. As the tubular members straighten and fill, the penis achieves its full diameter and is lifted into an erect position.

A primary objective of the present invention is to provide an erection enhancing prosthesis which can be implanted subcutaneously in the penis and is therefore later removable should complications arise, i.e., a reversible procedure may be performed without permanent damage to the penis.

A further objective is to increase the length and girth of the penis without causing structural damage to the penis.

Another objective is to provide a prosthesis capable of maintaining a smooth, natural look and feel, both while flaccid and while inflated.

A still further objective is to teach an improved mounting structure for the implant.

A final objective is to teach an improved operational orientation of the erectile member of the invention relative to its mounting base and source of hydraulic fluid.

Other features and advantages of the present invention will become apparent from the following more detailed description, taken in conjunction with the accompanying drawings, which illustrate, by way of example, the principles of the invention.

BRIEF DESCRIPTION OF THE DRAWING

The accompanying drawings illustrate the present invention. In such drawings.

DETAILED DESCRIPTION OF THE INVENTION

Figure 1:
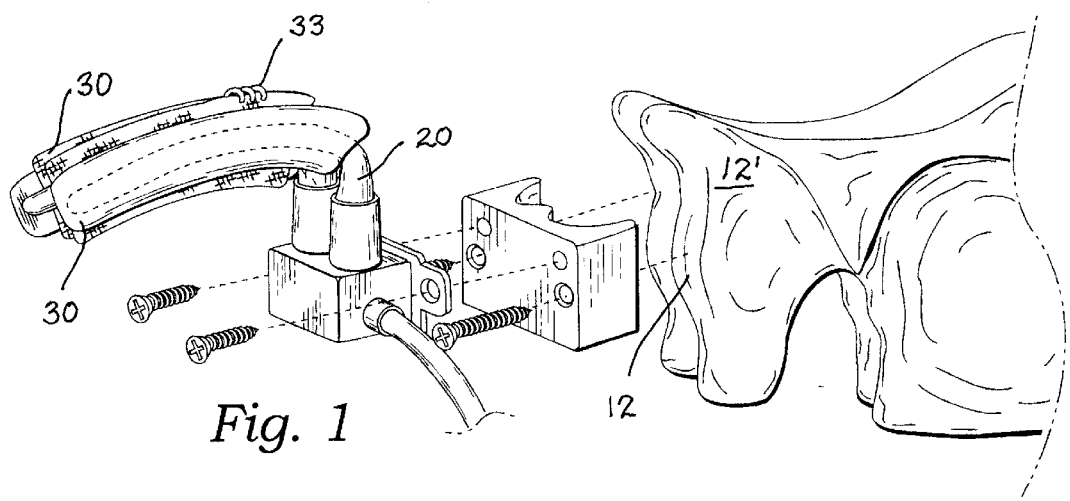
FIG. 1 is a perspective exploded view of the preferred embodiment of the present invention showing the penis in a semi erect state.

The above described drawing figures illustrate the invention, a penile prosthesis apparatus 5. The penile prosthesis apparatus 5 is adapted for subcutaneous insertion and operation within a penis 10 of an individual. It is designed to be anchored to the periosteum of the patient's pubic bone 12 and extends to the base of the glans penis 14. The prosthesis apparatus 5 fits above and to the outside of the corpus cavernosum 16 (see FIG. 4) opposite the corpus spongiosum 17 and under the outer skin 18 which covers the penis.

Figure 2:
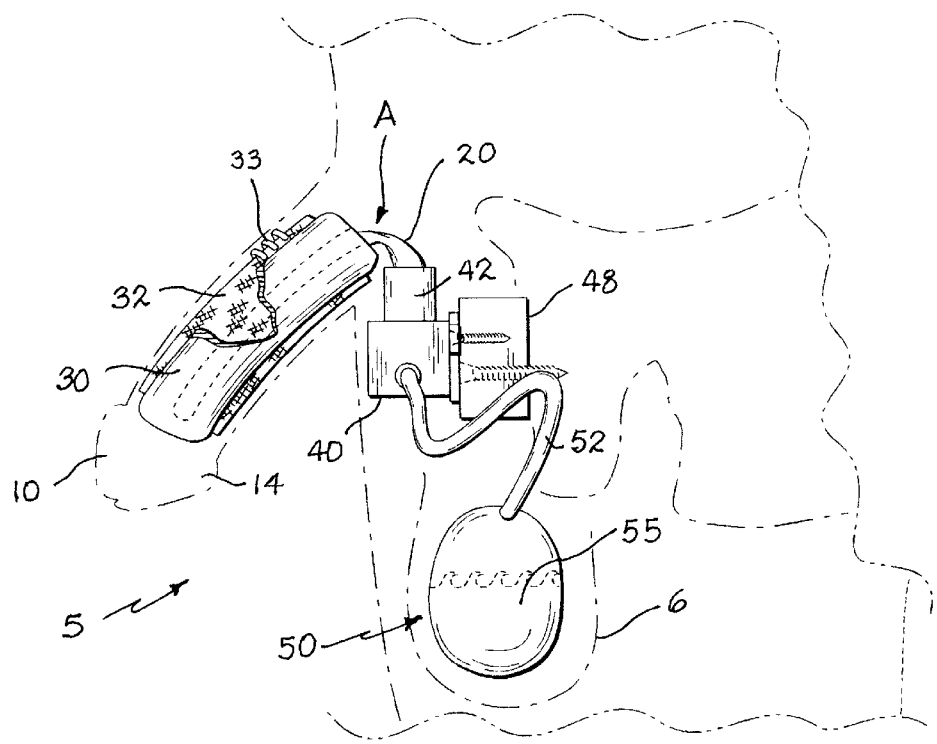
FIG. 2 is a side elevational view thereof, as assembled, and showing the penis in the flaccid state.
Figure 3:
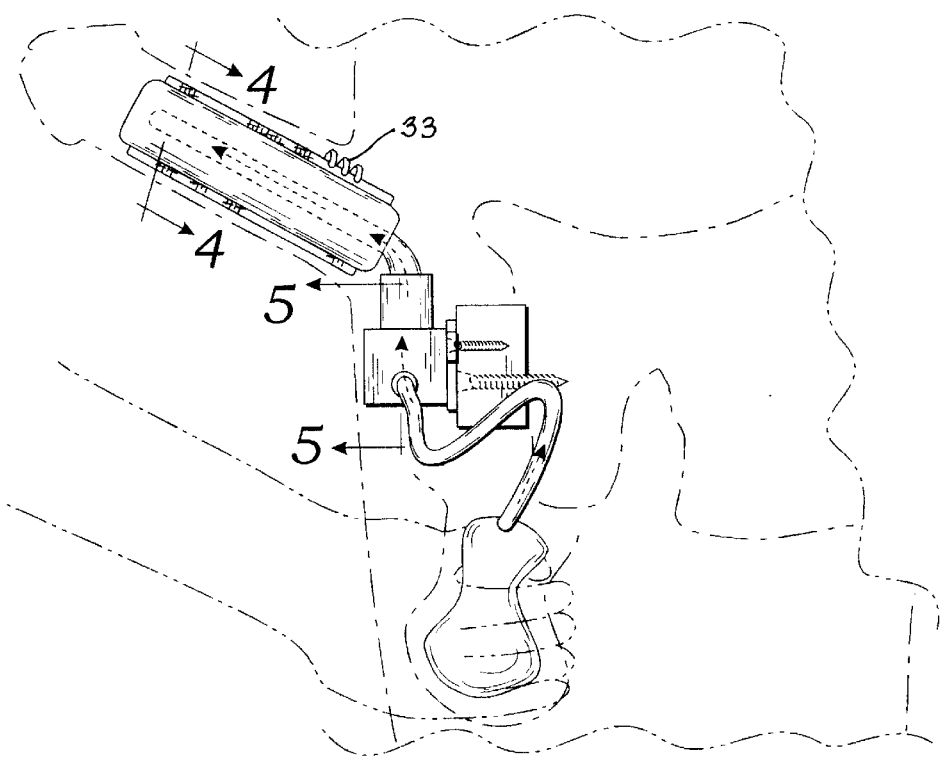
FIG. 3 is a side elevational view thereof showing the penis in the erect state and the means by which hydraulic pressure may be applied.
Figure 6:
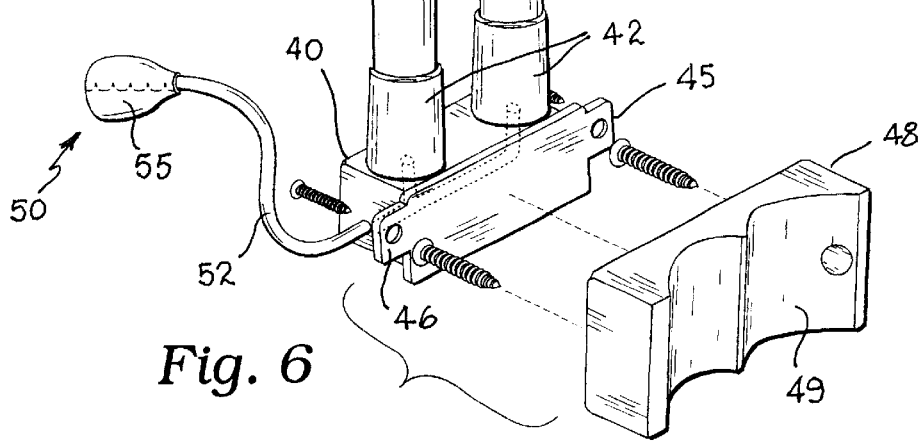
FIG. 6 is a perspective view showing the positional orientation of the invention as mounted relative to an upright individual and with the tubular members of the apparatus fully pressurized and showing one said member with a cover portion removed.

As seen in FIG. 6, the apparatus 5 comprises a shaped body portion 30 enabling, by its shape and size, an improved appearance and size to the penis 10, a tubular inflatable portion 20 enabling an erectile function of the penis 10, a mounting base portion 40 adapted for fluid interchange with the tubular inflatable portion 20, which is preferably two tubular members, through one or more of a fluid apertures 42 which are directed upwardly toward the upper torso of the individual host to the apparatus, and a fluid storage and pumping means 50 adapted for fluid interchange with the mounting base portion 40, and thereby to the tubular inflatable portion 20. As shown in FIGS. 2 and 3, the shaped body portion 30 and the tubular inflatable portion 20 are joined integrally and adapted in size and shape to lie aligned with the penis 10 below its outer skin 18. The fluid storage and pumping means 50 is enabled for moving a fluid 55 therefrom, where it is stored, to the tubular inflatable portion 20 through the fluid apertures 42 for pressurization thereof, the tubular inflatable portion 20 thereby assuming an approximately linear posture, as shown in FIG. 3 and an orientation similar to a naturally erect penis. The apparatus 5 is, therefore, directed to point toward the upper torso of the individual, the penis moving therewith.

Figure 4:
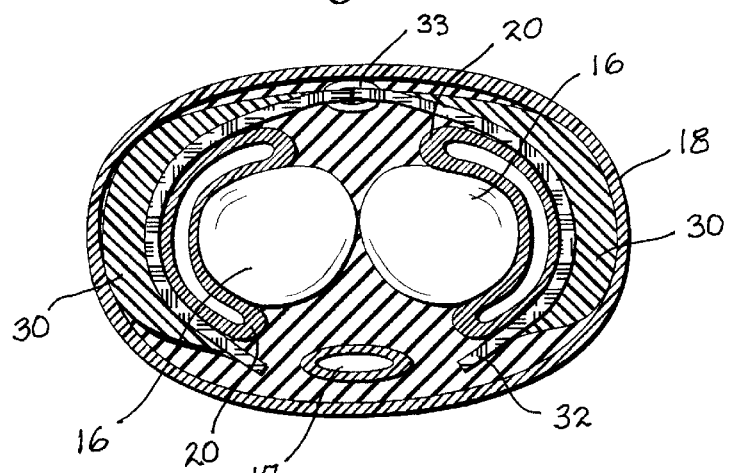
FIG. 4 is a sectional view thereof taken along line 4—4 in FIG. 3.

Preferably, the shaped body portion 30 and the tubular inflatable portion 20 comprise a left 22 and a right 24 halves thereof, spaced apart and positioned longitudinally at the upper left and the upper right quadrants of the penis 10 respectively as can be seen in FIG. 4 where the tubular inflatable portions 20 are shown in the deflated state. The shaped body portion 30 is comprised of a foam-like material encompassing a mesh fabric 32, the mesh fabric adapted, by its open weave, for gripping sutures 33 used for joining the shaped body portion 30 to the penis 10. The apparatus further comprises a rigid flange 45 integral with the mounting base portion 40, the flange providing opposing ears 46 extending laterally, each of the opposing ears 46 adapted with screw holes for receiving a mounting fastener such as the screws shown in FIG. 6. A mounting plate 48 provides a surface 49 contoured for close fitting to the pubic bone surface 12' for intimate contact in mounting thereto.

The inflatable tubular portion 20 is preferably made of a flexible bio-compatible material such as DACRON™ mesh fabric manufactured by DuPont. It is preferably 0.005–0.015 inches thick. As shown in FIGS. 2 and 3, when the prosthesis device 5 is surgically implanted, sutures 33 are used to secure the prosthesis device 5 into its proper position and such sutures 33 are engaged with the mesh fabric. The inflatable tubular portion 20 may be empty, but preferably it is stuffed with a porous silicone or foam silicone or similar material 21 which provides a degree of stiffness and support to the tubular portions 20 while allowing fluid to enter and leave the tubular portion 20 without being obstructed. The shaped body portion 30 is preferably made in accordance with U.S. Pat. No. 5,899,849 which is hereby incorporated into this application by reference. Integral with the inflatable tubular portion 20 is the mounting base portion 40 which is preferably made of molded silicone.

Figure 5:
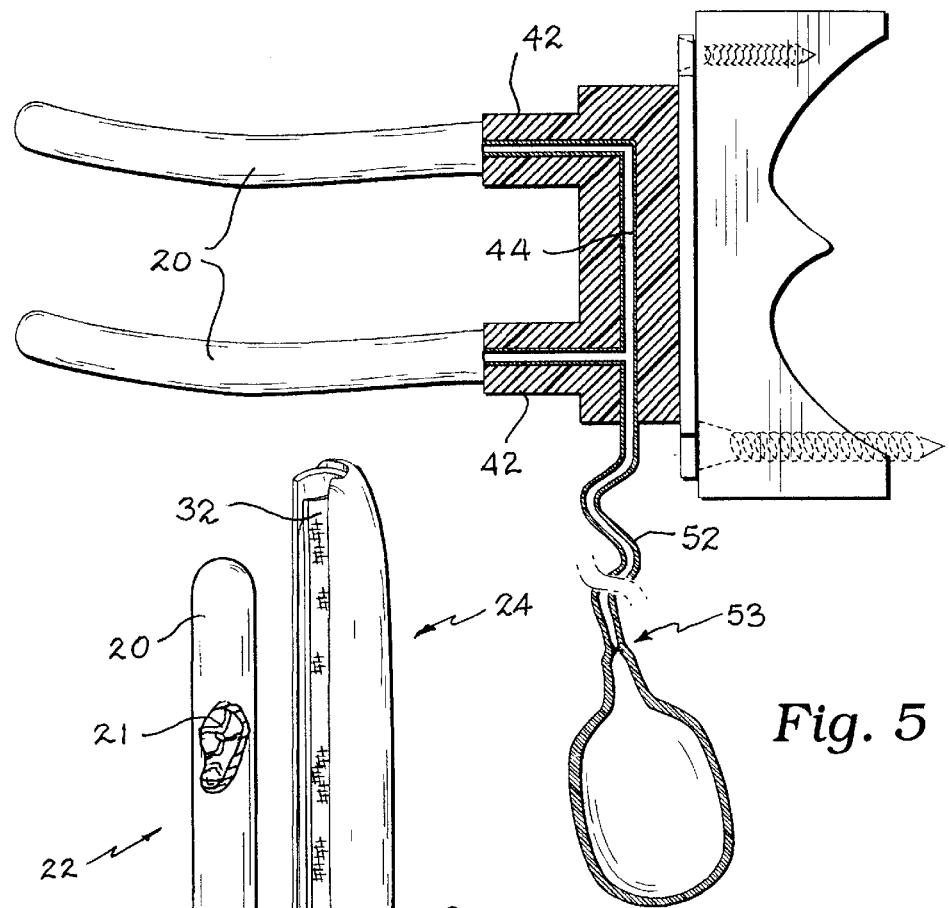
FIG. 5 is a hydraulic and mechanical schematic thereof.

The fluid storage and pumping means 50 preferably is implanted into the scrotum 6 and interconnected with mounting base portion 40 via tube 52. The fluid storage and pumping means 50 is shown schematically in FIG. 5. The tube 52 is preferably made of reinforced extruded silicone tube stock and is bio-compatible, soft and flexible, yet also is capable of withstanding the stress of pressurization enabled by one-way valve 53. A fluid 55, preferably a nontoxic substance such as saline solution, is pumped by the fluid storage and pumping means 50 through the tube 52, through the fluid conduit 44 of the mounting base portion 40 and into the inflatable tubular portion 20 for pressurization thereof so as to cause the tubular portion 20 to achieve rigidity. When in use, this causes the penis 10 to go from its flaccid state shown in FIG. 2, to an erect state shown in FIG. 3. Pressurizing the fluid 54 also serves to increase the diameter of the penis 10 as the inflatable tubular portion 20 expands. The fluid storage and pumping means 50 contains valve 53 which first allows the fluid 55 to be pumped into the inflatable tubular portion 20 to achieve the required pressurization, yet also can be reversed to allow the fluid 55 to drain back into the pump means 50, thereby deflating the inflatable tubular portion 20 so as to reverse the erection state. Such valves are well known in the art so that details are not further defined here.

The implant surgical procedure by which the above-described invention is implanted into a patient is well described in the incorporated reference. The procedure is fully reversible in that the prosthesis device may be removed from the penis with no lasting damage to the penis or its, adjacent tissues or organs. Instead of two inflatable assemblies or tubular portions 20, as shown in FIG. 4, the invention may be constructed having three or more such assemblies as the particular patient situation dictates.

A key inventive novelty teaching in the present invention is the orientation of the inflatable tubular portions 20 which are directed upwardly from the fluid apertures 42. This orientation, at first, seems to be counter intuitive. The '849 patent, for instance teaches that the portions 20 should extend horizontally from the mounting base portion 40. However, it has been discovered that when the portions 20 are joined to vertically directed fluid apertures 42 which are rigid, a significant improvement is achieved in the operation of the apparatus. In the flaccid state, shown in FIG. 2, the portions 20 bend into a kinked state, as shown at "A" in FIG. 2, thereby allowing the penis to be fully limp. When pressure is exerted by the pumping means 50, the section "A" of portion 20 immediately unkinks forcing the penis 10 to assume a semi-erect posture in preparation for full pressurization and erection.

While the invention has been described with reference to at least one preferred embodiment, it is to be clearly understood by those skilled in the art that the invention is not limited thereto. Rather, the scope of the invention is to be interpreted only in conjunction with the appended claims.

What is claimed is:

1. A penile prosthesis apparatus adapted for subcutaneous insertion and operation within a penis of an individual, the apparatus comprising: a shaped body portion enabling an improved appearance and size to the penis; a tubular inflatable portion enabling an erectile function of the penis; a mounting base portion adapted for fluid interchange with the tubular inflatable portion through a fluid aperture directed toward the upper torso of the individual; a fluid storage and pumping means adapted for fluid interchange with the mounting base portion; the shaped body portion and the tubular inflatable portion joined integrally and adapted in size and shape for subcutaneous insertion within the penis so as to lie aligned therewith below an outer skin of the penis; the fluid storage and pumping means enabled for moving a fluid therefrom, to the tubular inflatable portion through the fluid aperture for pressurization thereof, the tubular inflatable portion thereby assuming an approximately linear posture directed toward the upper torso of the individual, the penis moving therewith; the shaped body portion and tubular inflatable portion positioned orthogonally upwardly relative to a direction of mounting of the mounting base portion.

2. The device of claim 1 wherein the shaped body portion and the tubular inflatable portion comprise a left and a right halves thereof, spaced apart and centered longitudinally on the upper left and the upper right quadrants of the penis respectively.

3. The device of claim 1 wherein the shaped body portion is comprised of a foam-like material encompassing a mesh fabric, the mesh fabric adapted for gripping sutures for joining the shaped body portion to the penis.

4. The device of claim 1 further comprising a flange integral with the mounting base portion, the flange providing opposing ears extending laterally, each of the opposing ears adapted for receiving a mounting fastener.

5. The device of claim 1 further comprising a mounting plate, the mounting plate providing a surface contoured for close fitting to the pubic bone surface for intimate mounting thereto.

\* \* \* \* \*